United States Patent [19]

Lautenschläger et al.

[11] Patent Number: 4,565,659
[45] Date of Patent: Jan. 21, 1986

[54] SUBSTITUTED AMINOALKANOL PHOSPHOLIPIDS

[75] Inventors: Hans-Heiner Lautenschläger, Pulheim; Harald Borbe, Cologne; Gerrit Prop; Ferdinand Wirtz-Peitz, both of Pulheim; Ille-Stephanie Doppelfeld, Glessen; Michael J. Parnham, Pulheim, all of Fed. Rep. of Germany

[73] Assignee: A. Nattermann & Cie GmbH, Cologne, Fed. Rep. of Germany

[21] Appl. No.: 543,149

[22] Filed: Oct. 18, 1983

[30] Foreign Application Priority Data

Oct. 25, 1982 [DE] Fed. Rep. of Germany ....... 3239388
Oct. 25, 1982 [DE] Fed. Rep. of Germany ....... 3239390

[51] Int. Cl.$^4$ .............................................. C07F 9/10
[52] U.S. Cl. .............................................. 260/925
[58] Field of Search ...................... 260/925; 424/199

[56] References Cited

FOREIGN PATENT DOCUMENTS 0069968 1/1983 European Pat. Off. ............ 260/925

OTHER PUBLICATIONS

H. Mangold, "Angewandte Chemie", vol. 91, 550/556 (1979) and corresponding English Edition vol. 18, pp. 493–503.

H. Eibl, "Physical Structure to Therapeutic Applications", 1981 pp. 34–35.
H. Eibl, "Chemistry and Physics of Lipids", vol. 26 (1980), pp. 405–429.
N. T. Thoung et al., Bull. Soc. Chim. Fr. (1974) pp. 667–671.
N. S. Chandrakumar et al., Tetrahedron Letters, vol. 23, pp. 1043–1046 (1982).

*Primary Examiner*—Anton H. Sutto
*Attorney, Agent, or Firm*—Pearne, Gordon, Sessions, McCoy, Granger & Tilberry

[57] ABSTRACT

The invention concerns new substituted aminoalkanol phospholipids of the general Formula I

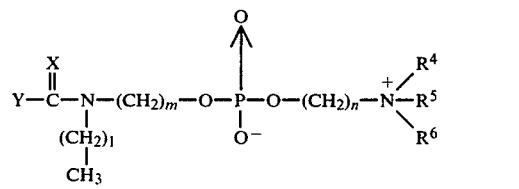

and methods for the treatment of humans suffering from high blood-pressure (hypertension), from inflammatory illnesses, from tumors and/or atherosclerosis by administering medicaments containing such a compound as well as methods for plant protections.

5 Claims, No Drawings

SUBSTITUTED AMINOALKANOL PHOSPHOLIPIDS

The present invention concerns new substituted aminoalkanol phospholipids and methods for using the same.

The compounds of the invention correspond to the general formula I

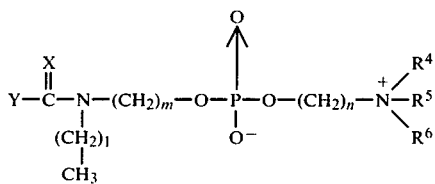

wherein X represents an oxygen or a sulphur atom and Y represents the radical $-NR^1R^2$ or $-OR^3$, wherein $R^1$, $R^2$ can be the same or can be different from each other and represent a saturated or unsaturated, straight-chained or branched alkyl radical having 1 to 20 carbon atoms, a benzyl radical, a phenyl radical or hydrogen; and $R^3$ stands for phenyl, benzyl or $C_{1-4}$-alkyl; $R^4$, $R^5$, $R^6$ can be the same or can be different from each other and stand for hydrogen or a low alkyl radical having 1 to 4 carbon atoms; l represents an integer from 0 to 19, m represents an integer from 2 to 6, and n an integer from 2 to 4.

Compounds according to the invention are, for example:

2-(3-hexadecyl-1-methylureido)-ethanol-phosphocholine
2-(1-methyl-3-octadecylureido)-ethanol-phosphocholine
2-(3-eicosyl-1-methylureido)-ethanol-phosphocholine
2-(1-methyl-3-oleylureido)-ethanol-phosphocholine
2-(3-methyl-1-undecylureido)-ethanol-phosphocholine
2-(3-ethyl-1-undecylureido)-ethanol-phosphocholine
2-(3,3-dimethyl-1-undecylureido)-ethanol-phosphocholine
2-(3-methyl-1-undecylthioureido)-ethanol-phosphocholine
2-(1-hexadecyl-3-methylureido)-ethanol-phosphocholine
2-(3-ethyl-1-hexadecylureido)-ethanol-phosphocholine
2-(1-hexadecyl-3-methylthioureido)-ethanol-phosphocholine
2-(3,3-dimethyl-1-hexadecylureido)-ethanol-phosphocholine
2-(3-methyl-1-octadecylureido)-ethanol-phosphocholine
2-(3-ethyl-1-octadecylureido)-ethanol-phosphocholine
2-(3,3-dimethyl-1-octadecylureido)-ethanol-phosphocholine
2-(3-methyl-1-octadecylthioureido)-ethanol-phosphocholine
2-(3-butyl-1-octadecylureido)-ethanol-phosphocholine
2-(3-hexadecyl-1-octadecylureido)-ethanol-phosphocholine
2-(3-benzyl-1-octadecylureido)-ethanol-phosphocholine
3-(3-methyl-1-octadecylureido)-propanol-(1)-phosphocholine
3-(3-ethyl-1-octadecylureido)-propanol-(1)-phosphocholine
3-(3,3-dimethyl-1-octadecylureido)-propanol-(1)-phosphocholine
3-(3-methyl-1-octadecylthioureido)-propanol-(1)-phosphocholine
4-(3-methyl-1-octadecylureido)-butanol-(1)-phosphocholine
4-(3-ethyl-1-octadecylureido)-butanol-(1)-phosphocholine
4-(3,3-dimethyl-1-octadecylureido)-butanol-(1)-phosphocholine
4-(3-methyl-1-octadecylthioureido)-butanol-(1)-phosphocholine
2-(1-eicosyl-3-methylureido)-ethanol-phosphocholine
2-(1-eicosyl-3-ethylureido)-ethanol-phosphocholine
2-(3,3-dimethyl-1-eicosylureido)-ethanol-phosphocholine
2-(1-eicosyl-3-methylthioureido)-ethanol-phosphocholine
2-(3-phenyl-1-undecylureido)-ethanol-phosphocholine
2-(3-benzyl-1-undecylureido)-ethanol-phosphocholine
2-(1-undecylureido)-ethanol-phosphocholine
2-(3-Hexadecyl-1-undecylureido)-ethanol-phosphocholine
2-(3-oleyl-1-undecylureido)-ethanol-phosphocholine
[2-(3-methyl-1-octadecylureido)-ethyl]-(2-triethylammonioethyl)-phosphate
[2-(3-methyl-1-octadecylureido)-ethyl]-(2-dimethylammonioethyl)-phosphate
N-benzyloxycarbonyl-N-methyl-2-aminoethanol-(1)-phosphocholine
N-benzyloxycarbonyl-N-undecyl-2-aminoethanol-(1-phosphocholine
N-benzyloxycarbonyl-N-hexadecyl-2-aminoethanol-(1)-phosphocholine
N-benzyloxycarbonyl-N-octadecyl-2-aminoethanol-(1)-phosphocholine
N-benzyloxycarbonyl-N-octadecyl-3-aminopropanol-(1)-phosphocholine
N-benzyloxycarbonyl-N-octadecyl-4-aminobutanol-(1)-phosphocholine
N-benzyloxycarbonyl-N-eicosyl-2-aminoethanol-(1)-phosphocholin
N-methoxycarbonyl-N-octadecyl-2-aminoethanol-(1)-phosphocholine
N-ethoxycarbonyl-N-octadecyl-2-aminoethanol-(1)-phosphocholine The compounds according to the invention are biologically very active and can be used, for example, in medicaments and plant protective preparations. The new compounds exhibit a strong pharmacological action. In particular, they exhibit a blood pressure reducing and immuno-regulating action. They can be used, therefor, for treating in particular hypertension, but also for treating inflammatory illnesses and for the therapy of atherosclerosis.

For producing the new ureidoalkyl phospholipids wherein l and m are as in Formula I, are reacted in an inert organic solvent, such as for example, ether, tetrahydrofuran, dioxane, acetone, chloroform, dimethylformamide, with a benzyl halide or chloroformic acid benzyl ester preferably in the presence of an auxiliary base, such as, for example, pyridine, dimethylaminopyridine, triethylamine, an alkali metal hydroxide, or alkaline earth metal oxide, to form compounds of the general Formula III.

The reaction may also be performed in two phases, possibly with the use of a phase-transfer catalyst. The compounds III wherein $R^7$ is benzyl and m is 2, can also be produced from N-benzylalkyl amines and ethylene oxide. The compounds II are obtainable either by the reaction of the appropriate amines with ethylene oxide or by the reduction of N-acyl-W-aminoalkanols.

The compounds of the general Formula III

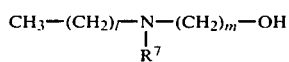  III wherein l and m are the same as in Formula I and $R^7$ represents a radical separable by hydrogenation, such as, for example, benzyl or benzyloxycarbonyl, are converted according to methods known per se to the phospholipids of the general Formula IV

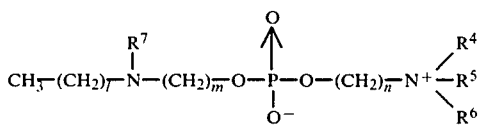  IV wherein $R^4$, $R^5$, $R^6$, l, m and n are the same as in Formula I and $R^7$ is the same as in Formula III. Compounds of Formula IV wherein $R^7$ is benzyloxycarbonyl correspond to compounds of Formula I wherein $R^3$ is benzyl. For example, the compounds III can be phosphonylated with dichlorophosphoric acid-ω-alkyl halide esters of Formula V

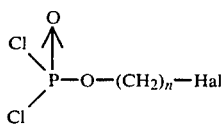  V wherein n is the same as in Formula I and Hal is a chlorine or bromine atom, in an inert organic solvent, possibly, using an auxiliary base, and the product can subsequently be reacted with an amine of Formula VI

  VI wherein $R^4$, $R^5$, $R^6$ are the same as in Formula I, in an inert organic solvent, possibly, under pressure, to form the compounds of Formula IV (see H. K. Mangold, Angew.Chem.. 91, 550–560 (1979); H. Eibl, Chem. and Phys. of Lipids, 26, 405–429 (1980).

The compounds of Formula IV can also be produced by reacting compounds of Formula III with phosphorus oxytrichloride and then with an alkane diol of Formula VII

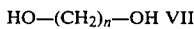  VII in which n is the same as in Formula I, possibly with the introduction of auxiliary bases, such as, for example, triethyl amine, and using inert solvents, such as, for example, tetrahydrofuran, to form cyclic intermediate products of Formula VIII

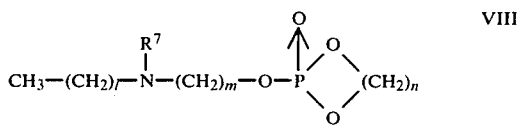  VIII wherein l, m, n and $R^7$ are the same as in Formula IV (see H. Eibl, 'Phospholipid Synthesis' in Knight (publisher), Liposomes, Elsevier 1981, pages 19–50).

The intermediate products of Formula VIII can also be prepared by reacting compounds of Formula III with a cyclic phosphor compound of Formula IX

  IX wherein n is the same as in Formula I, in an inert organic solvent with the addition of an auxiliary base [N. S. Chandrakumar et al., Tetrahedron Lett. 23, 1043–46, (1982); Biochim. Biophys. Acta 711, 357–360 (1982)].

The intermediate products VIII can be converted in a simple manner, for example, by treating with an amine of Formula VI in an organic solvent, possibly under pressure, to compounds of Formula IV (N. T. Thuong and P. Chabrier, Bull. Soc. Chim. Fr. 1974, 667–671).

The compounds of the Formula IV are hydrogenated with hydrogen in a suitable organic solvent, such as, eg, methanol, ethanol, ether dioxane or mixtures thereof and with water accompanied by separation of the benzyl group in the presence of a conventional hydrogenation catalyst, such as, for example, palladium/active carbon, whereby the compounds of the general Formula X

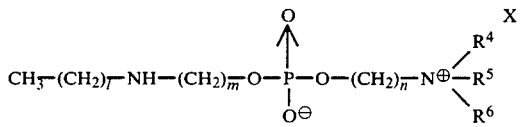  X wherein $R^4$, $R^5$, $R^6$, l, m and n are the same as in Formula I, develop.

The compounds of Formula X are reacted with carbonic acid derivatives of Formula XI or XII $R^1$—N=C=X  XI

  XII wherein $R^1$, $R^2$ and X are the same as in Formula I, either in substance or in an inert organic solvent, such as, eg, dimethylformamide, chloroform, N-methylacetamide, possibly with the addition of a catalyst, such as, eg, dimethylaminopyridine or of a base, such as, eg, pyridine, triethylamine, in particular when compounds of Formula XII are used, to form the compounds of Formula I of the invention.

The compounds of Formula I wherein $R^1$=$R^2$=H, can be produced suitably in aqueous or aqueous-organic media, such as, eg, water/dioxane, with the use of alkalicyanates, possibly with the addition of an organic or inorganic acid, preferably acetic acid, analogously to the known urea syntheses (see, eg, Weygand-Hilgetag, *Org. Chem. Experimentierkunst*, publishing house J. A. Barth-Leipzig, 1970, p.420) from compounds of Formula X.

The compounds of Formula I in which $R^1$=benzyl and $R_2$=H, and X=O can also be hydrogenated with hydrogen in a suitable organic solvent, such as, eg, methanol, ethanol, ether, dioxane or mixtures thereof and with water, accompanied by the separation of the benzyl group in the presence of a conventional hydrogenation catalyst, such as, eg, palladium/active carbon, whereby compounds of Formula I in which $R^1=R^2=H$ develop.

For producing the new (aryl)alkyloxy carbonyl aminoalkanol phospholipids of Formula I, N-alkyl-amino alcohols of Formula II are reacted in an inert organic solvent, such as, eg, ether, tetrahydrofuran, dioxane, acetone, chloroform, dimethyl formamide, with chloroformic acid benzyl ester, chloroformic acid phenyl ester or chloroformic acid alkyl ester, preferably in the presence of an auxiliary base, such as, eg, pyridine, dimethyl amino pyridine, triethyl amine, alkali hydroxide, alkaline earth oxide, to form compounds of the general Formula XIII

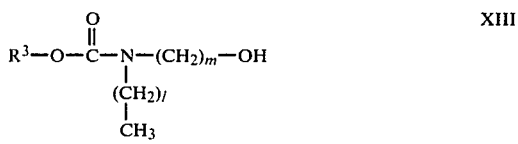

The compounds of Formula XIII wherein $R^3$, l and m are the same as in Formula I, are converted according to methods known per se to the phospholipids of the general Formula I.

The compounds of Formula XIII can be phosphorylated, eg, with dichlorophosphoric acid-ω-alkyl halide esters of Formula V in an indifferent organic solvent, possibly using an auxiliary base, and subsequently converted to compounds of Formula I by reacting with an amine of Formula VI in an indifferent organic solvent, possibly under pressure.

The compounds of formula I can also be prepared by phosphorylating compounds of Formula XIII with phosphorus oxytrichloride and subsequently converting the product with an alkane diol of Formula VII, possibly with the introduction of auxiliary bases, such as, eg, triethyl amine, and with the use of inert solvents, such as, eg, hydrofuran, and with the use of indert solvents, such as, eg, tetrahydrofuran, to cyclic intermediate products of Formula XIV

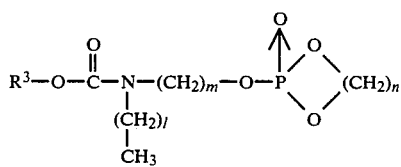

wherein l, m, n and $R^3$ are the same as in Formula I.

The intermediate products XIV can be converted to the compounds of Formula I in a simple manner, eg, by treating with an amine of Formula VI, in an organic solvent, possibly under pressure. The Compounds of Formula I can also be prepared by reacting compounds of of Formula X with chloroformic acid esters in inert solvents, such as, eg. chloroform, dimethyl formamide, possibly with the addition of an auxiliary base, such as, eg, pyridine, triethyl amine.

Suitable starting compounds of Formula II are, for example, the following compounds:

2-methylamino-ethanol, 2-ethylamino-ethanol, 2-Propylamino-ethanol, 2-butylamino-ethanol, 2-Pentylamino-ethanol, 2-hexylamino-ethanol, 2-heptylamino-ethanol, 2-octylamino-ethanol, 2-nonylamino-ethanol, 2-decylamino-ethanol, 2-undecylamino-ethanol, 2-dodecylamino-ethanol, 2-tridecylamino-ethanol, 2-tetradecylamino-ethanol, 2-pentadecylamino-ethanol, 2-hexadecylamino-ethanol, 2-heptadecylamino-ethanol, 2-octadecylamino-ethanol, 2-nondecylamino-ethanol, 2-eicosylamino-ethanol, 3-methylamino-propanol, 3-ethylamino-propanol, 3-propylamino-propanol, 3-butylamino-propanol, 3-pentylamino-propanol, 3-hexylamino-propanol, 3-heptylamino-propanol, 3-octylamino-propanol, 3-nonylamino-propanol, 3-decylamino-propanol, 3-undecylamino-propanol, 3-dodecylamino-propanol, 3-tridecylamino-propanol, 3-tetradecylamino-propanol, 3-pentadecylamino-propanol, 3-hexadecylamino-propanol, 3-heptadecylamino-propanol, 3-octadecylamino-propanol, 3-nonadecylamino-propanol, 3-eicosylamino-propanol, 4-methylamino-butanol, 4-ethylamino-butanol, 4-propylamino-butanol, 4-butylamino-butanol, 4-pentylamino-butanol, 4-hexylamino-butanol, 4-heptylamino-butanol, 4-octylamino-butanol, 4-nonylamino-butanol, 4-decylamino-butanol, 4-undecylamino-butanol, 4-dodecylamino-butanol, 4-tridecylamino-butanol, 4-tetradecylamino-butanol, 4-pentadecylamino-butanol, 4-hexadecylamino-butanol, 4-heptadecylamino-butanol, 4-nonadecylamino-butanol, 4-octadecylamino-butanol, 4-eicosylamino-butanol, 5-methylamino-pentanol, 5-ethylamino-pentanol, 5-propylamino-pentanol, 5-butylamino-pentanol, 5-pentylamino-pentanol, 5-hexylamino-pentanol, 5-heptylamino-pentanol, 5-octylamino-pentanol, 5-nonylamino-pentanol, 5-decylamino-pentanol, 5-undecylamino-pentanol, 5-dodecylamino-pentanol, 5-tridecylamino-pentanol, 5-tetradecylamino-pentanol, 5-pentadecylamino-pentanol, 5-hexadecylamino-pentanol, 5-heptadecylamino-pentanol, 5-octadecylamino-pentanol, 5-nonadecylamino-pentanol, 5-eicosylamino-pentanol, 6-methylamino-hexanol, 6-ethylamino-hexanol, 6-propylamino-hexanol, 6-butylamino-hexanol, 6-pentylamino-hexanol, 6-hexylamino-hexanol, 6-heptylamino-hexanol, 6-octylamino-hexanol, 6-nonylamino-hexanol, 6-decylamino-hexanol, 6-undecylamino-hexanol, 6-dodecylamino-hexanol, 6-tridecylamino-hexanol, 6-tetradecylamino-hexanol, 6-pentadecylamino-hexanol, 6-octadecylamino-hexanol, 6-hexadecylamino-hexanol, 6-heptadecylamino-hexanol, 6-nonadecylamino-hexanol, or 6-eicosylamino-hexanol.

Suitable starting compounds of Formula V include, for example:
dichlorophosphoric acid-2-bromethyl ester, dichlorophosphoric acid-2-chloroethyl ester, dichlorophosphoric acid-3-brompropyl ester, dichlorophosphoric acid-4-brombutyl ester.

Secondary and tertiary amines are preferably used as starting compounds of Formula VI, for example:
dimethyl amine, diethyl amine, dipropyl amine, dibutyl amine, trimethyl amine, triethyl amine, tripropyl amine, tributyl amine, ethyl methyl amine, methyl propyl amine, ethyl propyl amine, butylmethyl amine, butylethyl amine, butylpropyl amine, dimethylethyl amine, dimethylpropyl amine, butyldimethyl amine, diethylmethyl amine, diethylpropyl amine, butyldiethyl amine, dipropylmethyl amine, dipropylethyl amine, butyldipropyl amine, dibutylmethyl amine, dibutylethyl amine, dibutylpropyl amine, ethylmethylpropyl amine, butylmethylpropyl amine, butylethylmethyl amine, butylethylpropyl amine.

Suitable starting compounds of Formula XI include, for example:

methyliso cyanate, methylisothio cyanate, ethyliso cyanate, ethylisothio cyanate, propyliso cyanate, propylisothiocyanate, isopropyliso cyanate, isopropylisothio cyanate, butyliso cyanate, butylisothio cyanate, allyliso cyanate, allylisothio cyanate, hexyliso cyanate, hexylisothio cyanate, octyliso cyanate, octylisothio cyanate, decyliso cyanate, decyliosothio cyanate, undecyliso cyanate, undecylisothio cyanate, dodecyliso cyanate, dodecylisothio cyanate, tetradecyliso cyanate, tetradecylisothio cyanate, hexadecyliso cyanate, hexadecylisothio cyanate, octadecyliso cyanate, octadecylisothio cyanate, oleyliso cyanate, oleylisothio cyanate, eicosyliso cyanate, eicosylisothio cyanate, phenyliso cyanate, benzyliso cyanate, phenylisothio cyanate, benzyliosothiocyanate.

Preferred starting compounds of Formula XII are carbamic acid chlorides and thiocarbamic acid chlorides, the substituents $R^1$, $R^2$ of which contain a short-chain hydrocarbon chain having 1 to 4 carbon atoms, for example:

dimethyl carbamic acid chloride, diethyl carbamic acid chloride, dipropyl carbamic acid chloride, dibutyl carbamic acid chloride, methylethyl carbamic acid chloride, methylpropyl carbamic acid chloride, methylbutyl carbamic acid chloride, ethylpropyl carbamic acid chloride, butylpropyl carbamic acid chloride, butylethyl carbamic acid chloride, dimethylthio carbamic acid chloride, diethylthio carbamic acid chloride, dipropylthio carbamic acid chloride, dibutylthio carbamic acid chloride, methylethylthio carbamic acid chloride, methylpropylthio carbamic acid chloride, methylbutylthio carbamic acid chloride, ethylpropylthio carbamic acid chloride, butylpropyl carbamic acid chloride, butylethylthio carbamic acid chloride.

The new substituted aminoalkanol phospholipids can be processed, for example, to pharmaceutical preparations. These pharmaceutical preparations are suitable for enteral as well as oral or rectal and parenteral administration and contain the pharmaceutically active agents alone or together with a conventional, pharmaceutically applicable carrier material. The pharmaceutical preparation of the active agent is preferably in the form of individual doses which are adjusted to the desired administration, such as, eg, tablets, dragees, capsules, suppositories, granulates, solutions, emulsions or suspensions. The dose of the compounds is usually between 1 to 1000 mg per dose, preferably 1 to 10 mg per dose, and can be administered once or several times, preferably two to three times, daily.

The preparation of the compounds of the invention will now be explained in detail by way of the following examples:

A. Preparation of the alcohols of Formula III.

EXAMPLE 1

N-benzyloxycarbonyl-N-methyl-2-aminoethanol 75 g of 2-methylaminoethanol and 101 g of triethyl amine are mixed with 1000 ml of absolute chloroform. 171 g of chloroformic acid benzyl ester are added dropwise to this solution at about 20° C. The mixture is stirred for 1 hour at room temperature, washed with water, diluted hydrochloric acid and again with water and dried over sodium sulphate. After evaporation of the solvent in vacuo 173 g of oil remain.

Infrared (film): 1695 $cm^{-1}$.

EXAMPLE 2

N-benzyloxy carbonyl-N-undecyl-2-aminoethanol

Analogously to Example 1 from:
124 g of 2-undecylamino-ethanol
58 g of triethyl amine
500 ml of chloroform
97 g of chloroformic acid benzyl ester Purification by column chromatography (silica gel//hexane/acetic acid ethyl ester).

Yield: 113 g of oil with infrared (film): 1683 $cm^{-1}$.

EXAMPLE 3

N-benzyloxy carbonyl-N-hexadecyl-2-aminoethanol

Analogously to Example 1 from:
71 g of 2-hexadecylamino-ethanol
25 g of triethyl amine
250 ml of chloroform
43 g of chloroformic acid benzyl ester Purification by column chromatography (silica gel//chloform).

Yield: 40.2 g of oil with infrared (film): 1690 $cm^{-1}$.

EXAMPLE 4

N-benzyl-N-octadecyl-2-aminoethanol 40 ml of ethylene oxide cooled with dry ice are added dropwise into a mixture of 65.9 g of N-benzyl-octadecyl amine and 200 ml of methanol at room temperature within 2 hours; the mixture is stirred for further 3 hours, the solvent removed and the residue purified by column chromatography (silica gel//chloroform).

Yield: 73 g; melting point 31° C.

EXAMPLE 5

N-benzyloxy carbonyl-N-octadecyl-3-aminopropanol

Analogously to Example 1 from:
34.2 g of 3-octadecyl amino-propanol
10.5 g of triethyl amine
100 ml of chloroform
17.7 g of chloroformic acid benzyl ester Purification by column chromatography (silica gel//chloroform).

Yield: 33.1 g of oil with infrared (film): 1680 $cm^{-1}$.

EXAMPLE 6

N-benzyloxy carbonyl-N-octadecyl-4-aminobutanol

Analogously to Example 1 from:
24.8 g of 4-octadecylamino-butanol
7.4 g of triethyl amine
200 ml of chloroform
12.5 g of chloroformic acid benzyl ester Purification by column chromatography (silica gel//chloroform).

Yield: 18 g of oil with infrared (film): 1690 cm$^{-1}$.

EXAMPLE 7

N-benzyloxy carbonyl-N-eicosyl-2-aminoethanol

Analogously to Example 1 from:
32.8 g of 2-eicosylamino-ethanol
9.7 g of triethyl amine
200 ml of chloroform
16.3 g of chloroformic acid benzyl ester Purification by column chromatography (silica gel//hexane/acetic acid ethyl ester).

Yield: 14.6 g; melting point: 53°–54° C., infrared (film): 1690 cm$^{-1}$.

B. Preparation of the phospholipids of Formula IV.

EXAMPLE 8

N-benzyloxy carbonyl-N-methyl-2-aminoethanol-phosphocholine (a) 46 g of N-benzyloxy carbonyl-N-methyl-2-aminoethanol, dissolved in 220 ml of chloroform, are added dropwise into a mixture of 105 g of dichlorophosphoric acid-2-bromethyl ester, 53 ml of pyridine and 800 ml of abolute chloroform under cooling with ice. The reaction mixture is stirred for one hour while being cooled with ice and, after addition ice water, for another hour at room temperature. The organic phase is separated, washed with water until it is neutral, dried over sodium sulphate and reduced. The residue is purified by column chromatography (silica gel//chloroform/methanol).

Yield: 28 g of (N-benzyloxy carbonyl-N-methyl-2-aminoethyl)-2-bromethyl-phosphate (oil).

(b) 28 g of (N-benzyloxy carbonyl-N-methyl-2-eminoethyl)-2-bromethyl phosphate are dissolved in 300 ml of dry toluene, mixed with 30 ml of 33% ethanolic trimethyl amine solution and the mixture stirred for 4 hours at 60° C. in an autoclave. The solvents are then removed in a Rotavapor and the residue purified by column chromatography (silica gel//chloroform/methanol/water).

Yield: 8.5 g; melting point 75°–78° C.

EXAMPLE 9

N-benzyloxy carbonyl-N-undecyl-2-eminoethanol-phosphocholine

Analogously to Example 8 from:

(a)

75 g of dichlorophosphoric acid-2-bromethyl ester
51 ml of pyridine
600 ml of chloroform
54.2 g of N-benzyloxy carbonyl-N-undecyl-2-aminoethanol in 150 ml of chloroform.

Yield: 47.8 g of (N-benzyloxy carbonyl-N-undecyl-2-aminoethyl)-2-bromethyl-phosphate (oil).

(b)

47.6 g of (N-benzyloxy carbonyl-N-undecyl-2-eminoethyl)-2-bromethyl-phosphate
300 ml of toluene
30 ml of 33% ethanolic trimethyl amine solution Yield: 29.9 g; melting point: 224° to 226° C., infrared (in KBr): 1692 cm$^{-1}$.

EXAMPLE 10

N-benzyloxy carbonyl-N-hexadecyl-2-aminoethanol phosphocholine

Analogously to Example 8 from:

(a)

46 g of dichlorophosphoric acid-2-bromethyl ester
23 ml of pyridine
400 ml of chloroform
40 g of N-benzyloxy carbonyl-N-hexadecyl-2-aminoethanol in 95 ml of chloroform Yield: 21.5 g of (N-benzyloxy carbonyl-N-hexadecyl-2-aminoethyl)-2-bromethyl-phosphate (oil).

(b)

21.4 g of (N-benzyloxy carbonyl-N-hexadecyl-2-aminoethyl)-2-bromethyl-phosphate
100 ml of toluene
10 ml of 33% ethanolic trimethyl amine solution Yield: 7 g; melting point: 226° to 228° C., infrared (in KBr): 1691 cm$^{-1}$.

EXAMPLE 11

N-benzyl-N-octadecyl-2-aminoethanol-phosphocholine (a) 8.3 g of dichlorophosphoric acid-2-bromethyl ester are added dropwise into amixture of 10 g of N-benzyl-N-octadecyl-2-aminoethanol, 50 ml of chloroform and 5 g of triethyl amine, while being cooled with ice. The reaction mixture is stirred for further 3 hours at room temperature and, after adding ice water, again for 1 hour. The organic phase is separated, washed with water till neutral, dried over sodium sulphate and reduced. The residue is purified by column chromatography (silica gel//chloroform/methanol).

Yield: 9.2 g of (N-benzyl-N-octadecyl-2-aminoethyl)-2-bromethyl phosphate (oil).

(b) N-benzyl-N-octadecyl-2-aminoethanol-phosphocholine

Analogously to Example 8b from:
9.2 g of (N-benzyl-N-octadecyl-2-aminoethyl)-2-bromethyl phosphate
30 ml of toluene
5.2 ml of 33% ethanolic trimethyl amine solution Yield: 6.4 g; melting point: 215°–217° C.

EXAMPLE 12

N-benzyloxy carbonyl-N-octadecyl-3-aminopropanol-(1)-phosphochloine

Analogously to Example 8 from:

(a)

34.3 g of dichlorophosphoric acid-2-bromethyl ester
140 ml of pyridine
140 ml of chloroform
32.7 g of N-benzyloxy carbonyl-N-octadecyl-3-aminopropanol in 100 ml of chloroform Yield: 9.6 g of (N-benzyloxy carbonyl-N-octadecyl-3-aminopropyl)-2-bromethyl-phosphate (oil).

(b)

9.5 g of (N-benzyloxy carbonyl-N-octadecyl-3-aminopropyl)-2-bromethyl-phosphate
45 ml of toluene
5 ml of 33% ethanolic trimethyl amine solution Yield: 6.5 g; melting point: 219°–223° C., infrared (in KBr): 1688 cm$^{-1}$.

EXAMPLE 13

N-benzyloxy carbonyl-N-octadecyl-4-aminobutanol-(1)-phosphocholine

Analogously to Example 8 from (a)

17.4 g of dichlorophosphoric acid-2-bromethyl ester
72 ml of pyridine
72 ml of chloroform
17 g of N-benzyloxy carbonyl-N-octadecyl-4-aminobutanol in 40 ml of chloroform Yield: 6.1 g of (N-benzyloxy carbonyl-N-octadecyl-4-aminobutyl)-2-bromethyl-phosphate (oil).

(b)

6 g of (N-benzyloxy carbonyl-N-octadecyl-4-aminobutyl)-2-bromethyl-phosphate
30 ml of toluene
3 ml of 33% ethanolic trimethyl amine solution Yield: 4 g; melting point: 220° C. (decomposition), infrared (in KBr): 1694 cm$^{-1}$.

EXAMPLE 14

N-benzyloxy carbonyl-N-eicosyl-2-aminoethanol-phosphocholine

Analogously to Example 8 from:

(a)

14.5 g of dichlorophosphoric acid-2-bromethyl ester
7.5 ml of pyridine
120 ml of chloroform
14.5 g of N-benzyloxy carbonyl-N-eicosyl-2-aminoethanol in 30 ml of chloroform Yield: 12.7 g of (N-benzyloxy carbonyl-N-eicosyl-2-aminoethyl)-2-bromethyl-phosphate (oil).

(b)

12.6 g of (N-benzyloxy carbonyl-N-eicosyl-2-aminoethyl)-2-bromethyl-phosphate
60 ml of toluene
20 ml of 33% ethanolic trimethyl amine solution Yield: 11.4 g; melting pont: 210° C. (decomposition), infrared (in KBr): 1694 cm$^{-1}$.

EXAMPLE 15

(N-benzyl-N-octadecyl-2-aminoethyl)-2-triethylammonioethyl phosphate

Analogously to Example 8b from
11.8 g of (N-benzyl-N-octadecyl-2-aminoethyl)-2-bromethyl phosphate
60 ml of toluene
5 ml of triethyl amine and
10 ml of 2-propanol Yield: 10.2 g; melting point: 215°–216° C.

EXAMPLE 16

(N-benzyl-N-octadecyl-2-aminoethyl)-2-dimethylammonioethyl phosphate

Analogously to Example 8b from:
11.8 g of (N-benzyl-N-octadecyl-2-aminoethyl)-2-bromethyl phosphate
60 ml of toluene and 30 ml of 2-propanol
10 ml of 40% aqueous dimethyl amine solution Yield: 9.5 g; melting point: 210° C.

C. Preparation of the phospholipids of Formula X

EXAMPLE 17

2-methylaminoethanol phosphocholine 8 g of N-benzyloxy carbonyl-N-methyl-2-aminoethanol phosphocholine are dissolved in 60 ml of dioxane and 15 ml of water; the solution is mixed with 0.8 g of 10% palladium active carbon and the reaction mixture hydrogenated with hydrogen. After the H$_2$-absorption has terminated, the solution is filtered and the filtrate reduced in vacuo to dryness.

Yield: 5 g of a wax-like substance.

EXAMPLE 18

3-undecylamino ethanol phosphocholine

Analogously to Example 17 from:
14 g of N-benzyloxy carbonyl-N-undecyl-2-aminoethanol phosphocholine and
1.4 g of Pd active carbon in dioxane/water (ratio: 4:1; V/V)

Yield: 9.2 g; melting point: 205° to 208° C.

EXAMPLE 19

2-hexadecylamino ethanol phosphocholine

Analogously to Example 17 from:
6.9 g of N-benzyloxy carbonyl-N-hexadecyl-2-aminoethanol phosphocholine and
0.7 g of Pd-active carbon in dioxane/water (ratio 4:1; V/V)

Yield: 5.2 g; melting point: 203° to 207° C. (decomposition).

EXAMPLE 20

2-octodecylamino ethanol phosphocholine

Analogously to Example 17 from:
6.4 g of N-benzyl-N-octadecyl-2-aminoethanol phosphocholine and
0.6 g of Pd-active carbon in dioxane/water (ratio 4:1; V/V)

Yield: 5 g; melting point: 210° to 212° C.

EXAMPLE 21

8-octadecylamino propanol phosphocholine

Analogously to Example 17 from:
6.2 g of N-benzyloxy carbonyl-N-octadecyl-3-aminopropanol phosphocholine and
0.6 g of Pd-active carbon in dioxane/water (ratio: 4:1; V/V)

Yield: 4.4 g; melting point; 227° to 229° C.

EXAMPLE 22

4-octadecylamino butanol phosphocholine

Analogously to Example 17 from:
3.7 g of N-benzyloxy carbonyl-N-octadecyl-4-aminobutanol phosphocholine and
0.4 g of Pd-active carbon in dioxane/water (ratio 4:1; V/V)
Yield: 2.2 g; melting point: 208° to 210° C.

EXAMPLE 23

2-eicosylamino ethanol phosphocholine

Analogously to Example 17 from:
11 g of N-benzyloxy carbonyl-N-eicosyl-2-aminoethanol phosphocholine and
1.1 g of Pd-active carbon in dioxane/water (ratio: 4:1; V/V)
Yield: 7.4 g; melting point: 214° to 219° C.

EXAMPLE 24

(N-octadecyl-2-aminoethyl)-2-triethylammonioethyl phosphate

Analogously to Example 17 from:
10 g of (N-benzyl-N-octadecyl-2-aminoethyl)-2-triethylammonioethyl phosphate and
1 g of Pd-active carbon in dioxane/water (ratio: 4:1; V/V)
Yield: 8.1 g; melting point: 218° to 219° C.

EXAMPLE 25

(N-octadecyl-2-aminoethyl)-2-dimethylammonioethyl phosphate

Analogously to Example 17 from:
9.3 g of (N-benzyl-N-octadecyl-2-aminoethyl)-2-dimethylammonioethyl phosphate and
0.9 g of Pd-active carbon in dioxane/water (ratio: 4:1; V/V)
Yield: 7.5 g; melting point: 220° to 223° C.

D. Preparation of the phospholipids of Formula I

EXAMPLE 26

2-(3-ethyl-I-octadecylureido)-ethanol phosphocholine 0.5 g of 2-octadecylamino-ethanol phosphocholine are dissolved in 10 ml of chloroform, the solution is mixed with 0.14 g of ethylisocyanate and a few drops of dimethyl formamide and stirred for about 4 hours at room temperature. The solution is reduced in vacuo and the residue purified by column chromatography (silica gel//chloroform/methanol/water).
Yield: 0.43 g; melting point: 214° to 215° C., infrared (in KBr): 1630, 1535 cm$^{-1}$.

EXAMPLE 27

2-(3-methyl-1-octadecylureido)-ethanol phosphocholine

Analogously to Example 26 from:
0.5 g of 2-octadecylamino-ethanol phosphocholine
0.11 g of methylisocyanate
10 ml of chloroform
Yield: 0.35 g; melting point: 219° to 220° C., infrared (in KBr): 1625, 1540 cm$^{-1}$.

EXAMPLE 28

2-(3-methyl-1-octadecylthioureido)-ethanol phosphocholine

Analogously to Example 26 from:
0.5 g of 2-octadecylamino ethanol phosphocholine
0.15 g of methylisothiocyanate
10 ml of chloroform
Yield: 0.41 g; melting point: 215° to 217° C.

EXAMPLE 29

2-(3,3-dimethyl-1-octadecylureido)-ethanol phosphocholine 0.5 g of 2-octadecylamino-ethanol phosphocholine is dissolved in 10 ml of chloroform, the solution is mixed with 0.21 g of dimethyl carbamic and 0.14 g of silver carbonate and stirred for about 12 hours at room temperature. The solution is reduced in vacuo and the residue purified by column chromatography (silica gel//chloroform/methanol/water).
Yield: 0.31 g; melting point: 215° to 216° C., infrared (in KBr) 1634 cm$^{-1}$.

EXAMPLE 30

2-(3-butyl-1-octadecylureido)-ethanol phosphocholine

Analogously to Example 26 from:
0.5 g of 2-octadecylamino-ethanol phosphocholine
0.2 g of butylisocyanate
10 ml of chloroform
Yield: 0.38 g; melting point: 208° to 210° C., infrared (in KBr): 1625, 1530 cm$^{-1}$.

EXAMPLE 31

2-(3-hexadecyl-1-octadecylureido)-ethanol phosphocholine

Analogously to Example 26 from:
0.5 g of 2-octadecylamino-ethanol phosphocholine
0.6 g of hexadecylisocyanate
10 ml of chloroform
Yield: 0.63 g; melting point: 220° to 203° C., infrared (in KBr): 1625, 1535 cm$^{-1}$.

EXAMPLE 32

2-(3-benzyl-1-octadecylureido)-ethanol phosphocholine

Analogously to Example 26 from:
0.5 g of 2-octadecylamino-ethanol phosphocholine
0.27 g of benzylisocyanate
10 ml of chloroform
Yield: 0.42 g; melting point: 221° to 222° C.

EXAMPLE 33

2-(3-methyl-1-undecylureido)-ethanol phosphocholine

Analogously to Example 26 from:
0.5 g of 2-undecylamino-ethanol phosphocholine
0.15 g of methylisocyanate
10 ml of chloroform
Yield: 0.3 g of wax-like substance with clarification temperature of ~185° C., infrared (in KBr): 1629, 1540 cm$^{-1}$.

EXAMPLE 34

2-(3-ethyl-1-undecylureido)-ethanol phosphocholine

Analogously to Example 26 from:
0.5 g of 2-undecylamino ethanol phosphocholine
0.18 g of ethyleisocyanate 10 ml of chloroform
Yield: 0.3 g of wax-like substance with clarification temperature of ~180° to 183° C., infrared (in KBr): 1626, 1536 cm$^{-1}$.

EXAMPLE 35

2-(3,3-dimethyl-1-undecylureido)-ethanol phosphocholine

Analogously to Example 29 from:
0.5 g of 2-undecylamino-ethanol-phosphocholine
0.28 g of dimethyl carbamic acid chloride
0.18 g of silver carbonate
10 ml of chloroform
Yield: 0.32 g of wax-like substance with clarification temperature of 203° to 204° C., infrared (in KBr): 1634 cm$^{-1}$.

EXAMPLE 36

2-(3-methyl-1-undecylthioureido)-ethanol phosphocholine

Analogously to Example 26 from:
0.5 g of 2-undecylamino-ethanol phosphocholine
0.19 g of methylisothiocyanate
10 ml of chloroform
Yield: 0.33 g of wax-like substance with clarification temperature of ~165° C.

EXAMPLE 37

2-(3-phenyl-1-undecylureido)-ethanol phosphocholine

Analogously to Example 26 from:
0.5 g of 2-undecylamino-ethanol phosphocholine
0.31 g of phenylisocyanate
10 ml of chloroform
Yield: 0.61 g of wax-like substance, infrared (in KBr): 1649, 1538 cm$^{-1}$.

EXAMPLE 38

2-(3-benzyl-1undecylureido)-ethanol phosphocholine

Analogously to Example 26 from:
1.5 g of 2-undecylamino-ethanol phosphocholine
1.1 g of benzylisocyanate
30 ml of chloroform
Yield: 1.7 g of wax-like substance, infrated (in KBr): 1533, 1628 cm$^{-1}$.

EXAMPLE 39

2-(3-hexadecyl-1-undecylureido)-ethanol phosphocholine

Analogously to Example 26 from:
0.5 g of 2-undecylamino-ethanol phosphocholine
0.7 g of hexadecylisocyanate
10 ml of chloroform
Yield: 0.69 g; melting point 196° to 199° C., infrared (in KBr): 1622, 1533 cm$^{-1}$.

EXAMPLE 40

2-(3-oleyl-1-undecylureido)-ethanol phosphocholine

Analogously to Example 26 from:
0.5 g of 2-undecylamino-ethanol phosphocholine
0.8 g of oleylisocyanate
10 ml of chloroform under nitrogen
Yield: 0.61 g of wax-like substance.

EXAMPLE 41

2-(1-hexadecyl-3-methylureido)-ethanol phosphocholine

Analogously to Example 26 from:
0.3 g of 2-hexadecylamino-ethanol phosphocholine
0.08 g of methylisocyanate
5 ml of chloroform
Yield: 0.22 g; melting point 215° to 218° C., infrared (in KBr): 1635, 1540 cm$^{-1}$.

EXAMPLE 42

2-(3-ethyl-1-hexadecylureido)-ethanol phosphocholine

Analogously to Example 26 from:
0.5 g of 2-hexadecylamino-ethanol phosphocholine
0.15 g of ethylisocyanate
10 ml of chloroform
Yield: 0.45 g; melting point 213° to 217° C.

EXAMPLE 43

2-(1-hexadecyl-3-methylthioureido)-ethanol phosphocholine

Analogously to Example 26 from:
0.5 g of 2-hexadecylamino-ethanol phosphocholine
0.16 g of methylisothiocyanate
10 ml of chloroform
Yield: 0.2 g; melting point: 210° to 212° C.

EXAMPLE 44

2-(3,3-dimethyl-1-hexadecylureido)-ethanol phosphocholine

Analogously to Example 29 from:
0.3 g of 2-hexadecylamino-ethanol phosphocholine
0.24 g of dimethylcarbamic acid chloride
0.1 g of silver carbonate
5 ml of chloroform
Yield: 0.15 g; melting point 208° to 211° C., infrared (in KBr): 1635 cm$^{-1}$.

EXAMPLE 45

3-(3-methyl-1-octadecylureido)-propanol-(1)-phosphocholine

Analogously to Example 26 from:
0.5 g of 3-octadecylamino-propanol-(1)-phosphocholine
0.11 g of methylisocyanate
10 ml of chloroform
Yield: 0.43 g; melting point: 221° to 224° C., infrared (in KBr): 1628, 1540 cm$^{-1}$

EXAMPLE 46

3-(3-ethyl-1-octadecylureido)-propanol-(1)-phosphocholine

Analogously to Example 26 from:
0.5 g of 3-octadecylamino-propanol-(1)-phosphocholine
0.14 g of ethylisocyanate
10 ml of chloroform
Yield: 0.3 g; melting point 215° to 218° C., infrared (in KBr): 1626, 1535 cm$^{-1}$.

EXAMPLE 47

3-(3,3-dimethyl-1-octadecylureido)-propanol-(1)-phosphocholine

Analogously to Example 29 from:
0.5 g of 3-octadecylamino-propanol-(1)-phosphocholine
0.18 g of dimethyl carbamic acid chloride 0.14 g of silver carbonate
10 ml of chloroform Yield: 0.28 g; melting point: 224° to 225° C., infrared (in KBr): 1633 cm$^{-1}$.

EXAMPLE 48

3-(3-methyl-1-octadecylthioureido)-propanol-(1)-phosphocholine

Analogously to Example 26 from:
0.5 g of 3-octadecylamino-propanol-(1)-phosphocholine
0.15 g of methylisothiocyanate
10 ml of chloroform Yield: 0.36 g; melting point: 210° to 212° C.

EXAMPLE 49

4-(3-methyl-1-octadecylureido)-butanol-(1)-phosphocholine

Analogously to Example 26 from:
0.5 g of 4-octadecylamino-butanol-(1)-phosphocholine
0.11 g of methylisocyanate
10 ml of chloroform Yield: 0.4 g; melting point: 226° to 230° C., infrared (in KBr): 1629, 1541 cm$^{-1}$.

EXAMPLE 50

4-(3-ethyl-1-octadecylureido)-butanol-(1)-phosphocholine

Analogously to Example 26 from:
0.3 g of 4-octadecylamino-butanol-(1)-phosphocholine
0.1 g of ethylisocyanate
5 ml of chloroform Yield: 0.25 g; melting point 215° to 216° C., infrared (in KBr): 1623, 1532 cm$^{-1}$.

EXAMPLE 51

4-(3,3-dimethyl-1-octadecyl)-butanol-(1)-phosphocholine

Analogously to Example 29 from:
0.3 g of 4-octadecylamino-butanol-(1)-phosphocholine
0.13 g of dimethyl carbamic acid chloride
0.1 g of silver carbonate
5 ml of chloroform Yield: 0.15 g; melting point: 234° to 236° C., infrared (in KBr): 1632 cm$^{-1}$.

EXAMPLE 52

4-(3-methyl-1-octadecylthioureido)-butanol-(1)-phosphocholine

Analogously to Example 26 from:
0.3 g of 4-octadecylamino-butanol-(1)-phosphocholine
0.1 g of methylisothiocyanate
10 ml of chloroform Yield: 0.21 g; melting point 221° to 224° C.

EXAMPLE 53

2-(1-eicosyl-3-methylureido)-ethanol-phosphocholine

Analogously to Example 26 from:
0.5 g of 2-eicosylamino-ethanol-phosphocholine
0.11 g of methylisocyanate
10 ml of chloroform Yield: 0.35 g; melting point: 222° to 224° C.

EXAMPLE 54

2-(1-eicosyl-3-ethylureido)-ethanol-phosphocholine

Analogously to Example 26 from:
0.5 g of 2-eicosylamino-ethanol-phosphocholine
0.14 g of ethylisocyanate
10 ml of chloroform Yield: 0.4 g; melting point: 218° to 220° C.

EXAMPLE 55

2-(3,3-dimethyl-1-eicosylureido)-ethanol-phosphocholine

Analogously to Example 29 from:
0.5 g of 2-eicosylamino-ethanol-phosphocholine
0.21 g of dimethyl carbamide acid chloride
0.14 g of silver carbonate
10 ml of chloroform Yield: 0.3 g; melting point: 215° to 217° C.

EXAMPLE 56

2-(1-eicosyl-3-methylthioureido)-ethanol-phosphocholine

Analogously to Example 26 from:
0.5 g of 2-eicosylamino-ethanol-phosphocholine
0.15 g of methylisothiocyanate
10 ml of chloroform Yield: 0.3 g; melting point: 210° to 211° C.

EXAMPLE 57

2-(1-undecylureido)-ethanol-phosphocholine

Analogously to Example 17 from:
1.2 g of 2-(3-benzyl-1-undecylureido)-ethanol-phosphocholine, and
0.72 g of Pd-active carbon which is added in 6 portions within 20 hours, in dioxane/water at a ratio of 4:1 (V/V).

Yield: 0.5 g of wax-like substance, infrared (in KBr): 1652, 1597 cm$^{-1}$.

EXAMPLE 58

[2-(3-methyl-1-octadecylureido)-ethyl]-(2-triethylammonio-ethyl)-phosphate

Analogously to Example 26 from:
0.5 g of (N-octadecyl-2-aminoethyl)-2-triethylammonio-ethyl-phosphate
0.11 g of methylisocyanate
10 ml of chloroform Yield: 0.41 g: melting point: 220° to 221° C.

EXAMPLE 59

[2-(3-methyl-1-octadecylureido)-ethyl]-(2-dimethylammonio-ethyl)-phosphate

Analogously to Example 26 from:
0.5 g of (N-octadecyl-2-aminoethyl)-2-dimethylammonio-ethylphosphate
0.11 g of methylisocyanate
10 ml of chloroform Yield: 0.35 g; melting point 215° to 216° C.

EXAMPLE 60

2-(3-hexadecyl-1-methylureido)-ethanol-phosphocholine 0.5 g of 2-methylamino-ethanol-phosphocholine is dissolved in 10 ml of N-methylacetamide; the solution is mixed with 1.08 g of hexadecyl-isocyanate and stirred for 24 hours at room temperature. The solution is reduced in vacuo and the residue purified by column chromatography (silica gel//chloroform/methanol/water).

Yield: 0.3 g; melting point: 210° to 213° C.

Analogously to Example 60 the following compounds are prepared:
2-(1-methyl-3-octadecylureido)-ethanol-phosphocholine
2-(3-eicosyl-1-methylureido)-ethanol-phosphocholine
2-(1-methyl-3-oleylureido)-ethanol-phosphocholine

EXAMPLE 61

N-methoxycarbonyl-N-octadecyl-2-aminoethanol-(1)-phosphocholine 50 ml of N-octadecyl-2-aminoethanol-(1)-phosphocholine are dissolved in 2 ml of chloroform; 20 mg of chloroformic acid methyl ester and 5 drops of triethyl amine are added. The mixture is stirred for one hour at room temperature, reduced in vacuo and the residue purified by column chromatography (silica gel//chloroform/methanol/water).

Yield: 41 mg of a wax-like substance, infrared (in KBr): 1692 cm$^{-1}$.

EXAMPLE 62

N-ethoxycarbonyl-N-octadecyl-2-aminoethanol-(1)-phosphocholine

Analogously to Example 61 from:
50 mg of N-octadecyl-2-aminoethanol-(1)-phosphocholine
20 mg of chloroformic acid ethyl ester
5 drops of triethylamine in 2 ml of chloroform Yield: 39 mg of a wax-like substance, infrared (in KBr): 1690 cm$^{-1}$.

EXAMPLE 63

N-benzyloxy carbonyl-N-octadecyl-2-aminoethanol-(1)-phosphocholine

Analogously to Example 61 from:
50 mg of N-octadecyl-2-aminoethanol-(1)-phosphocholine
34 mg of chloroformic acid benzyl ester
5 drops of triethylamine in 2 ml of chloroform.

Yield: 55 mg; melting point: 211° C.

What we claim is:

1. Substituted aminoalkanol phospholipids of the general Formula I

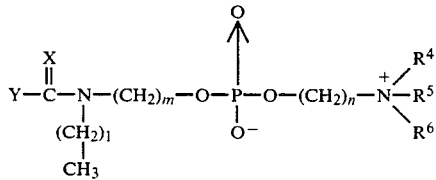

in which
X represents an oxygen or a sulphur atom and
Y the radical —NR$^1$R$^2$ or —OR$^3$,
wherein
R$^1$, R$^2$ can be the same or different and represent a saturated or unsaturated, straight-chained or branched alkyl radical having 1 to 20 carbon atoms, a benzyl radical, a phenyl radical or hydrogen,
R$^3$ represents phenyl, benzyl or C$_{1-4}$-alkyl
R$^4$, R$^5$, R$^6$ can be the same or different and represent hydrogen or a low alkyl radical having 1 to 4 carbon atoms,
l represents an integer from 0 to 19
m represents an integer from 2 to 6
n represents an integer from 2 to 4.

2. Substituted aminoalkanol phospholipids of the general Formula I according to claim 1 in which
X represents an oxygen or a sulphur atom and
Y the radical —NR$^1$R$^2$,
wherein
R$^1$,R$^2$ can be the same or different and represent a saturated or an unsaturated, straight-chained or branched alkyl radical having 1 to 20 carbon atoms, a benzyl radical, a phenyl radical or hydrogen;
R$^4$,R$^5$,R$^6$ can be the same or different and represent hydrogen or a low alkyl radical having 1 to 4 carbon atoms;
l represents an integer from 0 to 19;
m represents an integer from 2 to 6; and
n represents an integer from 2 to 4.

3. Substituted aminoalkanol phosphocholines of the general Formula I according to claim 1, in which
X represents an oxygen or a sulphur atom and
Y the radical NR$^1$R$^2$,
wherein
R$^1$,R$^2$ can be the same or different and represent an alkyl radical having 1 to 20 carbon atoms,
R$^4$,R$^5$,R$^6$ each represent a methyl group,
l an integer from 0 to 19
m an integer from 2 to 6 and
n represents 2.

4. Substituted aminoalkanol phospholipids of the general Formula I according to claim 1, in which
X represents an oxygen atom and
Y the radical —OR$^3$,
wherein
R$^3$ represents phenyl, benzyl or C$_{1-4}$-alkyl;
R$^4$,R$^5$,R$^6$ can be the same or different and represent hydrogen or a low alkyl radical having 1 to 4 carbon atoms;
l represents an integer from 0 to 19
m an integer from 2 to 6, and
n an integer from 2 to 4.

5. Substituted aminoalkanol phosphocholines of the general Formula I according to claim 1, in which
X represents an oxygen atom and
Y the radical —OR$^3$,
wherein
R$^3$ represents benzyl or C$_{1-4}$-alkyl,
R$^4$,R$^5$,R$^6$ each represent a methyl group,
l represents an integer from 0 to 19,
m an integer from 2 to 6, and
n represents 2.

* * * * *